US008258121B2

(12) United States Patent
Mentlik et al.

(10) Patent No.: US 8,258,121 B2
(45) Date of Patent: Sep. 4, 2012

(54) GLYCERYL AND GLYCOL ACID COMPOUNDS

(75) Inventors: Anton A. Mentlik, Dallas, TX (US); James Swanzy, Arlington, TX (US)

(73) Assignee: Mary Kay Inc., Dallas, TX (US)

( * ) Notice: Subject to any disclaimer, the term of this patent is extended or adjusted under 35 U.S.C. 154(b) by 0 days.

(21) Appl. No.: 13/038,074

(22) Filed: Mar. 1, 2011

(65) Prior Publication Data

US 2011/0294762 A1 Dec. 1, 2011

Related U.S. Application Data

(63) Continuation of application No. 11/749,869, filed on May 17, 2007, now Pat. No. 7,932,417.

(60) Provisional application No. 60/747,760, filed on May 19, 2006.

(51) Int. Cl.
*A61K 8/02* (2006.01)
*A61K 31/60* (2006.01)
*A01N 37/36* (2006.01)

(52) U.S. Cl. ........................................ 514/159; 424/401
(58) Field of Classification Search .................. 424/401; 514/159

See application file for complete search history.

(56) References Cited

U.S. PATENT DOCUMENTS

| | | | |
|---|---|---|---|
| 2,081,117 A | 5/1937 | Hall | 424/60 |
| 2,113,374 A | 4/1938 | Hall | 562/473 |
| 2,279,468 A | 4/1942 | Lahousse et al. | 424/60 |
| 3,949,087 A | 4/1976 | Bacq et al. | 514/561 |
| 4,009,254 A | 2/1977 | Renold | 424/59 |
| 4,723,420 A | 2/1988 | Sitte | 62/51.1 |
| 4,839,159 A | 6/1989 | Winter et al. | 424/59 |
| 5,045,306 A | 9/1991 | Cavazza et al. | 424/54 |
| 5,258,552 A | 11/1993 | Cavazza et al. | 564/197 |
| 5,314,689 A | 5/1994 | Scandurra et al. | 424/433 |
| 5,637,305 A | 6/1997 | Cavazza et al. | 424/401 |
| 5,667,791 A | 9/1997 | Hersh et al. | 424/401 |
| 5,827,886 A | 10/1998 | Hersh | 514/562 |
| 5,843,476 A | 12/1998 | Ribier et al. | 424/450 |
| 5,853,705 A | 12/1998 | Nakayama et al. | 424/59 |
| 5,925,369 A | 7/1999 | Scafetta et al. | 424/405 |
| 5,962,000 A | 10/1999 | Yanagida et al. | 424/401 |
| 6,051,245 A | 4/2000 | Chaudhry et al. | 424/401 |
| 6,284,234 B1 | 9/2001 | Niemiec et al. | 424/78.07 |
| 6,337,320 B1 | 1/2002 | Hersh et al. | 514/18 |
| 6,372,791 B1 | 4/2002 | Shapiro et al. | 514/557 |
| 6,376,557 B1 | 4/2002 | Zaveri | 424/725 |
| 6,432,424 B1 | 8/2002 | Shapiro et al. | 424/401 |
| 6,495,126 B1 | 12/2002 | Schlitz | 424/78.02 |
| 6,497,889 B2 | 12/2002 | Takekoshi et al. | 424/401 |
| 6,573,299 B1 | 6/2003 | Petrus | 514/558 |
| 6,585,987 B1 | 7/2003 | Fransoni | 424/401 |
| 6,649,176 B1 | 11/2003 | Shapiro et al. | 424/401 |
| 6,761,903 B2 | 7/2004 | Chen et al. | 424/451 |
| 6,762,158 B2 | 7/2004 | Lukenbach et al. | 510/122 |
| 6,835,392 B2 | 12/2004 | Hsu et al. | 424/449 |
| 6,908,889 B2 | 6/2005 | Niemiec et al. | 510/130 |
| 6,984,390 B2 | 1/2006 | Sakuta | 424/401 |
| 6,987,120 B1 | 1/2006 | Del Soldato | 514/365 |
| 2003/0147968 A1 | 8/2003 | Farber | 424/523 |
| 2003/0157137 A1 | 8/2003 | Farber | 424/401 |
| 2004/0146539 A1 | 7/2004 | Gupta | 424/401 |
| 2004/0161435 A1 | 8/2004 | Gupta | 424/401 |
| 2004/0191330 A1 | 9/2004 | Keefe et al. | 424/638 |
| 2005/0069598 A1 | 3/2005 | Ribnicky et al. | 424/740 |
| 2005/0100519 A1 | 5/2005 | Guth et al. | 424/62 |
| 2005/0158258 A1 | 7/2005 | Fisher | 424/63 |
| 2005/0214333 A1 | 9/2005 | Lanzendoerfer et al. | 424/401 |
| 2005/0220728 A1 | 10/2005 | Kanji et al. | 424/59 |
| 2005/0261242 A1 | 11/2005 | Soldato | 514/56 |
| 2005/0266057 A1 | 12/2005 | Hagura et al. | 424/443 |
| 2006/0002876 A1 | 1/2006 | Cahen | 424/70.1 |
| 2006/0029657 A1 | 2/2006 | Popp et al. | 424/450 |
| 2011/0159126 A1* | 6/2011 | Tai | 424/758 |

FOREIGN PATENT DOCUMENTS

| | | |
|---|---|---|
| DE | 126311 | 11/1901 |
| EP | 1421940 | 5/2004 |
| FR | 1254002 | 1/1961 |
| GB | 2283173 | 5/1995 |
| RU | 2294167 | 9/2006 |
| WO | WO 02/26207 | 4/2002 |

OTHER PUBLICATIONS

Djurendic et. al. (CAS accession # 2000:779843, corresponding to Djurendic et. al., Journal of the Serbian Chemical Society (2000), 65:681-689).*
Djurendic et al., CAS accession No. 2000:779843, corresponding to Djurendic et al., Journal of the Serbian Chemical Society, 65:681-689, 2000.
International Preliminary Report on Patentability, issued in Int. App. No. PCT/US2007/069160, mail date Dec. 4, 2008.
Ishihara et al., "An extremely simple, convenient, and selective method for acetylating primary alcohols in the presence of secondary alcohols," *Journal of Organic Chemistry*, 58:3791-3793, 1993.
Office Communication, issued in Chinese Patent Application No. 200780018364, dated Aug. 4, 2010. (English Translation).
Office Communication, issued in Eurasian Patent Application No. 200802364, dated Mar. 5, 2011. (English Summary).
Office Communication, issued in European Patent Application No. 07 762 239.7, dated Oct. 11, 2010.
Office Communication, issued in European Patent Application No. 07 762 239.7, dated Mar. 18, 2010.
Office Communication, issued in U.S. Appl. No. 11/749,869, dated Sep. 8, 2010.
Office Communication, issued in U.S. Appl. No. 11/749,869, dated Jun. 3, 2010.
Office Communication, issued in U.S. Appl. No. 11/749,869, dated Oct. 26, 2009.

(Continued)

Primary Examiner — Marcos Sznaidman
(74) *Attorney, Agent, or Firm* — Fulbright & Jaworski L.L.P.

(57) ABSTRACT

A composition comprising a glyceryl salicylate compound and/or a glycol salicylate compound. The compositions can be used to reduce the amount of moisture evaporated from skin, protect the skin from UV light, and treat aged or damaged skin.

6 Claims, No Drawings

OTHER PUBLICATIONS

Office Communication, issued in U.S. Appl. No. 11/749,869, dated Jun. 5, 2009.
Office Communication, issued in U.S. Appl. No. 11/749,869, dated Feb. 13, 2009.
Office Communication, issued in U.S. Appl. No. 11/749,869, dated Sep. 4, 2008.
PCT International Search Report and Written Opinion, issued in International Application No. PCT/US2007/069160, dated Oct. 23, 2007.
Office Communication issued in Ukrainian Patent Application No. 2008 14596, dated Aug. 2, 2011. (English translation).

* cited by examiner

GLYCERYL AND GLYCOL ACID COMPOUNDS

CROSS-REFERENCE TO RELATED APPLICATIONS

This application is a continuation of currently pending U.S. application Ser. No. 11/749,869 filed May 17, 2007, which claims the benefit of U.S. Provisional Application Ser. No. 60/747,760, filed May 19, 2006. The entire text of each of the above-referenced disclosures is specifically incorporated herein by reference without disclaimer.

BACKGROUND OF THE INVENTION

A. Field of the Invention

The present invention relates generally to a compound that can be used in compositions such as cosmetic skin care compositions. The compound can include an acid molecule attached to a glycerol or glycol molecule via an ester linkage.

B. Description of Related Art

With ageing, chronic exposure to adverse environmental factors, or malnutrition, the visual appearance, physical properties, and physiological functions of skin can change in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Several different approaches have been used to treat damaged skin caused by aging, environmental factors, chemicals, or malnutrition. These approaches can oftentimes have various drawbacks, such as significant irritation to the skin or skin toxicity.

SUMMARY OF THE INVENTION

The present invention overcomes deficiencies in the art. In a non-limiting aspect, the invention relates generally to compounds that can be used in compositions such as cosmetic and pharmaceutical compositions. In certain embodiments, the compound can include an acid molecule attached to a glyceryl or glycol molecule via an ester linkage. Generic and specific structures of these compounds are disclosed throughout this specification and incorporated into this section by reference.

In certain embodiments, the compounds can be incorporated into a composition. The composition can be cosmetic composition or a pharmaceutical composition. The composition can be topically applied to skin. The compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both.

In certain embodiments, the compositions of the present invention can include from about 0.001% to about 20%, by weight or volume, of glyceryl/acid or glycol/acid compounds, or a combination of both. It should be recognized, however, that the amount of the compounds in a composition can be modified below, within, or above this range based on the desired results (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 96, 97, 98, 99%, or more, by weight or volume of the composition). Therefore, the amount of a glyceryl/acid or glycol/acid compound can include less than 0.001% or more than 5%, by weight or volume. In other aspects, the compositions can include 0.002, 0.003, 0.004 . . . 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of glyceryl or glycol salicylate or a combination of both. In other embodiments, the compositions of the present invention can further include a carnitine molecule. The carnitine molecule can be acylated (e.g., acetyl-1-carnitine). In certain aspects, the ratio of any ingredient within the composition when compared to another ingredient can be from about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 50:1, 60:1, 70:1, 80:1, 90:1, 100:1, or more or any number derivable therein, by weight or volume of the total composition. In other aspects, the ratio of any ingredient within the composition when compared to another ingredient can be from about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:50, 1:60, 1:70, 1:80, 1:90, 1:100, or more or any number derivable therein, by weight or volume of the total composition.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In other non-limiting aspects of the present invention, the compositions can further include a vitamin, a mineral, an essential fatty acid, an amino acid (including essential and non-essential amino acids), a flavinoid, and/or a protein, or a combination thereof. Non-limiting examples of vitamins include the B vitamins (e.g., B1, B2, B6, B12, niacin, folic acid, biotin, and pantothenic acid), vitamin C, vitamin D, vitamin E (e.g., tocopherol or tocopheryl acetate), vitamin A (e.g., palmitate, retinyl palmitate, or retinoic acid), and vitamin K. Non-limiting examples of minerals include iron, potassium, phosphorus, magnesium, manganese, selenium, and calcium. Non-limiting examples of essential fatty acids include Omega 3 (linolenic acid), Omega 6 (linoleic acid) and Omega 9 (oleic acid) essential fatty acid, or a combination thereof. Non-limiting examples of amino acids include essential amino acids (e.g., lysine, leucine, isoleucine, methionine, phenylalanine, threonine, tryptophan, valine, histidine, or arginine) and non-essential amino acids (e.g., serine, asparagine, glutamine, aspartic acid, glutamic acid, alanine, tyrosine, cysteine, glycine, or proline). Non-limiting examples of flavinoids include anthocyanin compounds (e.g., cyanidin-3-glucoside and cyanidin-3-rutinoside).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Also disclosed is a method of treating or preventing a skin condition comprising topical application of a composition comprising a glyceryl/acid compound and/or a glycol/acid compound, wherein the topical application of the composition treats the skin condition. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identify a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

The compositions of the present invention can also be used in methods for exfoliate the skin. This allows the user to shed dead skin cells and also encourages the skin's natural sloughing process. An advantage of this process is that it reveals and exposes "younger," fresher skin. The shedding process unclogs pores, keeps skin clean and helps reduce acne breakouts.

The methods of the present invention can also include topically applying an amount effective to: increase the stratum corneum turnover rate of the skin; decrease skin roughness; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin); enhance desmosomal degradation, leading to an increase in corneocyte desquamation; increase cytokines, hyaluronic acid, cell proliferation, collagen production and epidermal proliferation; normalize corneocyte cohesion; enhance lipid synthesis in the intercellular areas; target the sebum in the sebaceous glands; and activate fibroblasts.

The compositions of the present invention can also be used in a regimen alone or with other compositions (e.g., skin care compositions). For instance, the composition of the present invention can be applied in the morning and/or evening at predetermined intervals and/or amounts. Alternatively, the compositions of the present invention can be applied in the morning and a second skin care composition can be applied in the evening and vice versa.

Also disclosed are methods for using the glyceryl/acid compounds and glycol/acid compounds as moisturizing agents, film-forming agents, UV absorption agents, and/or skin treatment agents. For instance, the compounds can maintain and/or increase the hydration (such as water content) of skin. The compounds can also lubricate the skin. The compounds can form a film or barrier on the outer surface of the skin which can reduce or prevent the evaporation of water from the skin. In certain aspects, the film can have tactile properties which make the skin feel soft or smooth. The compounds can also be used as UV absorption agents and can be used in methods for increasing the UV absorption characteristics of a composition such as, for example, a sunscreen composition. The compounds can be used in methods for increasing the SPF of a sunscreen composition. In certain aspects, the compounds can be used to increase the efficiency of existing sunscreen products and/or sunscreen agents that are used in such products. Alternatively, the compounds can be used as a stand alone sunscreen agent. In certain embodiments, the compounds can be used in methods for reducing or preventing cosmetic compositions from chemical or physical deterioration that is induced by ultraviolet light. The compounds and/or compositions of the present invention can diffract or absorb a broad spectrum of UV radiation. For example, the compounds and/or compositions can absorb or diffract UVA (approximately 315 to 400 nm), UVB (approximately 280 to 315) and/or UVC (approximately 10 to 280 nm) light. In certain aspects, the compounds and/or compositions can absorb or diffract UV light ranging from about 1 to about 400 nm, or any integer or range therein (e.g., 2, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 399).

Also contemplated are kits that include the compositions of the present invention. In certain embodiments, the composition is comprised in a container. The container can be a bottle, dispenser, or package. The container can dispense a predetermined amount of the composition. In certain aspects, the compositions is dispensed in a spray or mist, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is contemplated that any embodiment discussed in this specification can be implemented with respect to any method or composition of the invention, and vice versa. Furthermore, compositions of the invention can be used to achieve methods of the invention.

The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups.

The term "alkoxy" includes a group having the structure —OR, where R is an alkyl group. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, etc.

The term "hydroxyalkyl" includes an alkyl group having at least one hydroxy group.

The term "about" or "approximately" are defined as being close to as understood by one of ordinary skill in the art, and in one non-limiting embodiment the terms are defined to be within 10%, within 5%, within 1%, and/or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can protect or improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Compounds of the present invention can be used in all types of cosmetic compositions/formulations for treating, preserving, or preventing the appearance of aged or damaged skin.

For instance, the compounds of the present invention can have a wide variety of uses in compositions that are applied to skin. Non-limiting examples include using the compounds as a moisturizing agent, a film-forming agent, a UV absorption agent, and a skin treatment agent. As a moisturizing agent, the compounds can help maintain and/or increase the hydration of skin, thereby making the skin softer and more pliable. The compounds can also act as lubricants for the skin to treat, reduce, or prevent skin flaking and dry skin.

As a film-forming agent, the compounds can be used to form a film or barrier on the outer surface of the skin. This can be beneficial to the skin by reducing or preventing the evaporation of water from the skin. Additionally, the film can have tactile properties that make the skin feel soft and smooth.

As a UV absorption agent, the compounds can be used to protect the cosmetic composition from chemical or physical deterioration induced by ultraviolet light. The compounds can also be used as a sunscreen agent in sunscreen compositions. The compounds can also increase the sun protection factor (SPF) of a sunscreen composition that already includes a sunscreen agent.

As a skin treatment agent, the compounds can be used as active ingredients in topical skin care compositions. Non-limiting examples of skin conditions that can be treated with the compounds of the present invention are disclosed throughout this specification.

These and other aspect of the invention are described in further non-limiting detail below.

A. Glyceryl/Acid and Glycol/Acid Compounds

1. Glyceryl/Acid Compounds

A glyceryl/acid compound of the present invention can be derived from glycerol molecule which has the following structure:

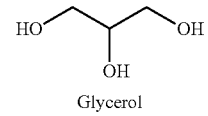

Glycerol

The acid portion of the glyceryl/acid compounds can be attached via an ester linkage of the OH group of the glycerol molecule and the COOH group of the acid molecule. In non-limiting aspects, a glyceryl/acid compound can have the following generic chemical structure:

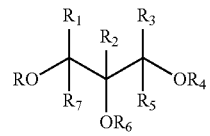

where R, $R_1$, $R_2$, $R_3$, $R_4$, $R_5$, and $R_6$ can each independently be an H, an acid molecule, a hydroxy, a halogen, an oxo (e.g., ether), an alkoxy, a silyloxy, an acyl, an aryl, an acetyl, a carbonyl, a cyano, a heterocyclyl, an amido, an aminocarbonyl, an amino, —NH-alkyl, —N(alkyl)$_2$, —NH-(substituted alkyl), —N-(substituted alkyl)$_2$, —NH-aryl, —N(aryl)$_2$, an azido, a trialkylsilyloxy, an acyloxy, a acylamino, a bis-acylamino, an ester, a NO, a NO$_2$, or a sulfo (e.g., thioether, thioester, thiocarbonyl, sulfonamido, sulfonyl, etc.). In certain aspects, the acid molecule is selected from the group consisting of salicylic acid, cinnamic acid, and benzoic acid, and derivatives and substituted acids thereof. Other non-limiting examples of acids that can be used in the context of the present invention are described in International Cosmetic Ingredient Dictionary and Handbook, 10$^{th}$ Ed., 2004, which is incorporated by reference. In certain aspects, at least one of R, $R_4$, and $R_6$ is an acid, R and $R_4$ are acids, R and $R_6$ are acids, $R_4$ and $R_6$ are acids, or R, $R_4$, and $R_6$ are all acids. Non-limiting examples of certain glyceryl/acid compounds of the present invention are illustrated below:

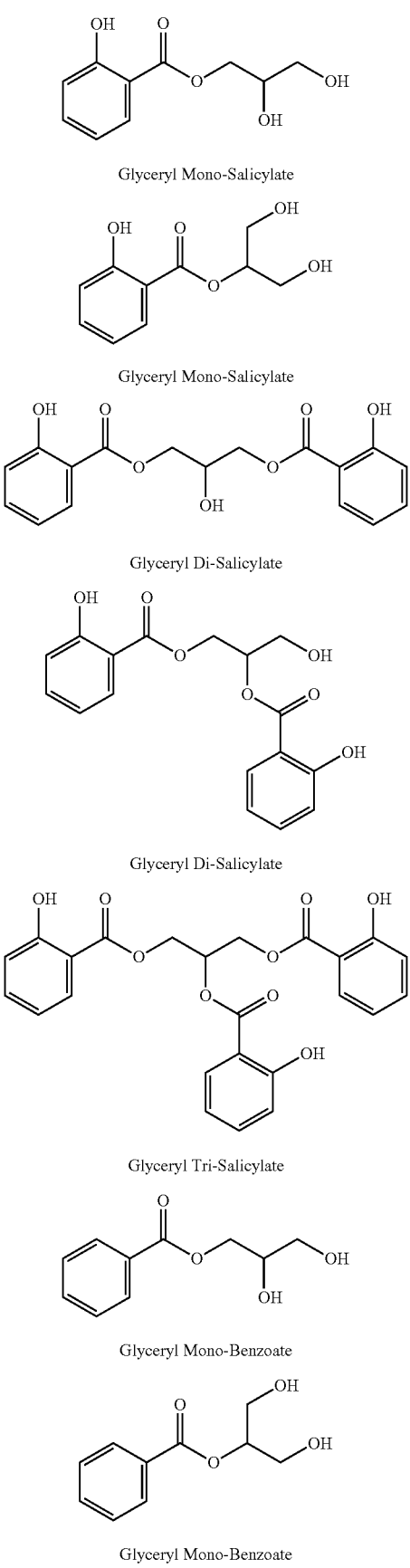
Glyceryl Mono-Salicylate
Glyceryl Mono-Salicylate
Glyceryl Di-Salicylate
Glyceryl Di-Salicylate
Glyceryl Tri-Salicylate
Glyceryl Mono-Benzoate
Glyceryl Mono-Benzoate
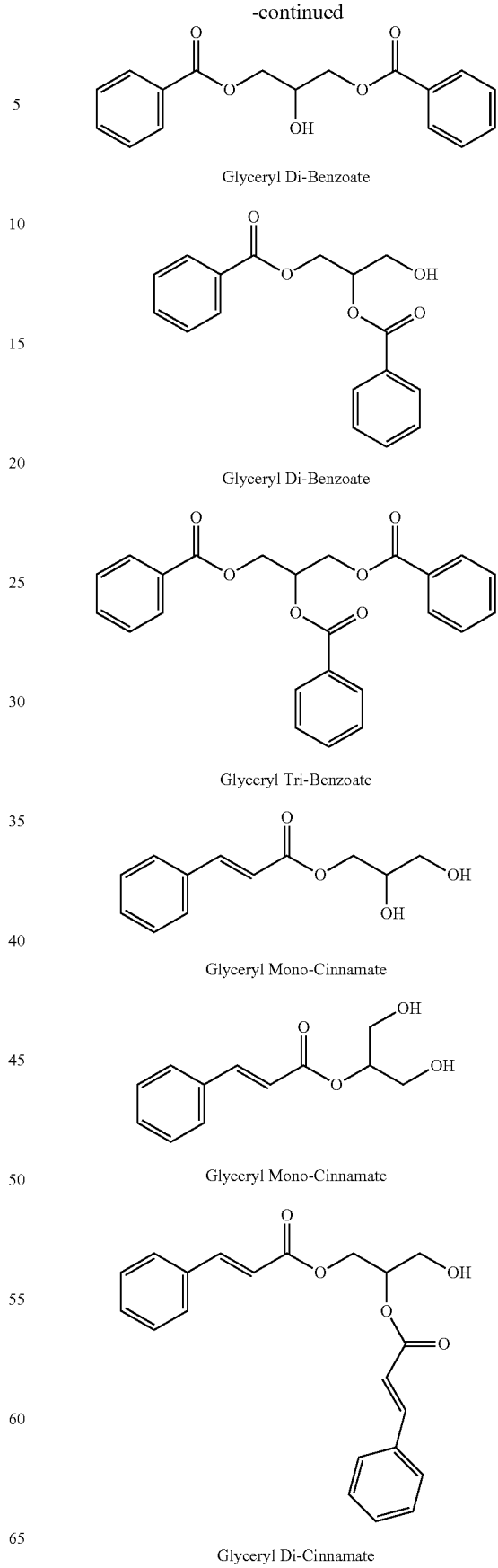
Glyceryl Di-Benzoate
Glyceryl Di-Benzoate
Glyceryl Tri-Benzoate
Glyceryl Mono-Cinnamate
Glyceryl Mono-Cinnamate
Glyceryl Di-Cinnamate -continued

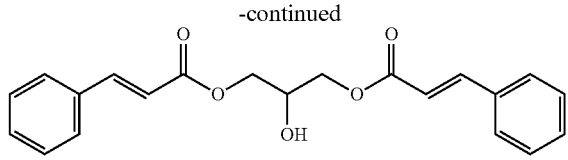

Glyceryl Di-Cinnamate

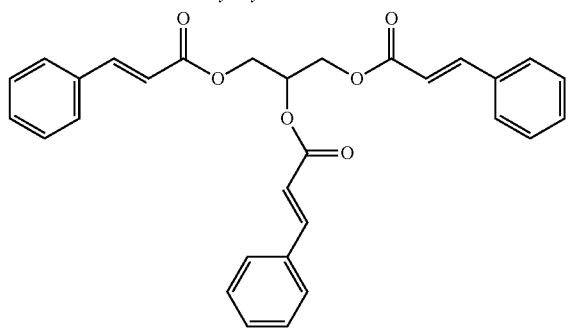

Glyceryl Tri-Cinnamate

The glyceryl/acid compounds and derivatives and modifications of the same can be prepared by using convention chemical synthesis techniques (see, e.g., Organic Chemistry, 5$^{th}$ Ed.).

2. Glycol/Acid Compounds

A glycol/acid compound of the present invention can be derived from a glycol molecule. Glycols are a generic class of dihydric alcohols. Non-limiting examples of glycols that can be used in the context of the present invention include: ethylene glycols (e.g., 1, 2 ethane diol (monoethylene glycol), 2-hydroxyethoxy)ethan-2-ol (diethylene glycol); polyethylene glycols (PEGs); propylene glycols (e.g., 1,2 propane diol, 1,3 propane diol, etc.); and butylene glycols (e.g., 1,2 butane diol, 1,3 butane diol, 1,4 butane diol, etc.). Other non-limiting examples of glycols that can be used in the context of the present invention are described in International Cosmetic Ingredient Dictionary and Handbook, 10$^{th}$ Ed., 2004, which is incorporated by reference. It certain aspects, the glycol that is used can have similar physical and chemical characteristics to glycerol.

The acid portion of the glycol/acid compounds can be attached via an ester linkage of the OH group of the glycol molecule and the COOH group of the acid molecule. In non-limiting aspects, a glycol/acid compound can have the following generic chemical structure:

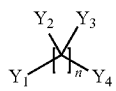

where n can be 2, 3, 4, 5, 6, 7, 8, 9, 10, or more, or any range therein. In certain aspects, n is an integer from 2 to 4. $Y_1$, $Y_2$, $Y_3$, and $Y_4$, can each independently be $OY_5$, an H, an acid molecule attached via an ester linkage, a hydroxy, a halogen, an oxo (e.g., ether), an alkoxy, a silyloxy, an acyl, an aryl, an acetyl, a carbonyl, a cyano, a heterocyclyl, an amido, an aminocarbonyl, an amino, —NH-alkyl, —N(alkyl)$_2$, —NH-(substituted alkyl), —N-(substituted alkyl)$_2$, —NH-aryl, —N(aryl)$_2$, an azido, a trialkylsilyloxy, an acyloxy, a acylamino, a bis-acylamino, an ester, a NO, a NO$_2$, or a sulfo (e.g., thioether, thioester, thiocarbonyl, sulfonamido, sulfonyl, etc.). In certain aspects, the acid molecule is selected from the group consisting of salicylic acid, cinnamic acid, and benzoic acid, and derivatives and substituted acids thereof. Other non-limiting examples of acids that can be used in the context of the present invention are described in International Cosmetic Ingredient Dictionary and Handbook, 10$^{th}$ Ed., 2004, which is incorporated by reference. $Y_5$ can be anyone of the groups identified for $Y_1$, $Y_2$, $Y_3$, and $Y_4$. In certain aspects $Y_5$ is an acid group. In other embodiments, at least two of $Y_1$, $Y_2$, $Y_3$, and $Y_4$ is a hydroxyl group. Non-limiting examples of certain particular glycol/acid compounds of the present invention are illustrated below:

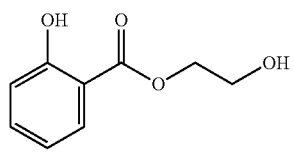

Ethylene Glycol Mono-Salicylate

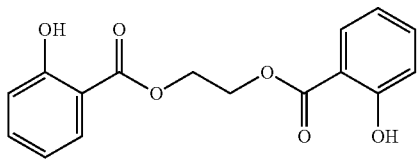

Ethylene Glycol Di-Salicylate

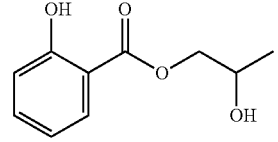

Propylene Glycol Mono-Salicylate

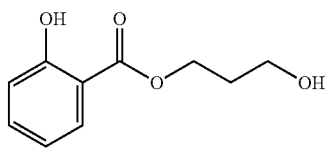

Propylene Glycol Mono-Salicylate

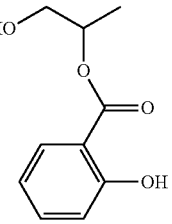

Propylene Glycol Mono-Salicylate

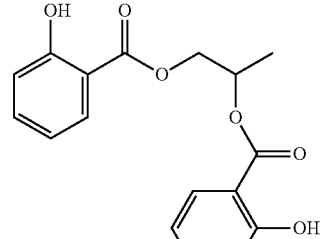

Propylene Glycol Di-Salicylate

11
-continued

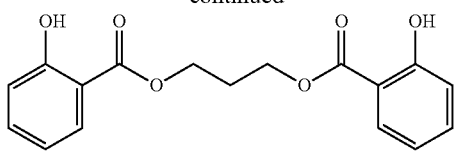

Propylene Glycol Di-Salicylate

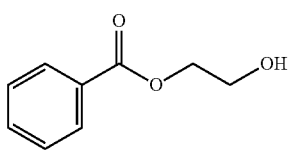

Ethylene Glycol Mono-Benzoate

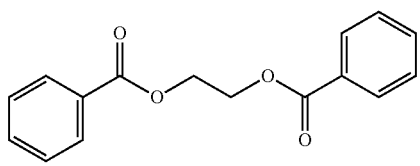

Ethylene Glycol Di-Benzoate

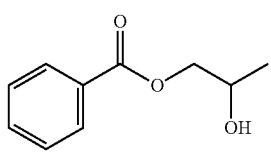

Propylene Glycol Mono-Benzoate

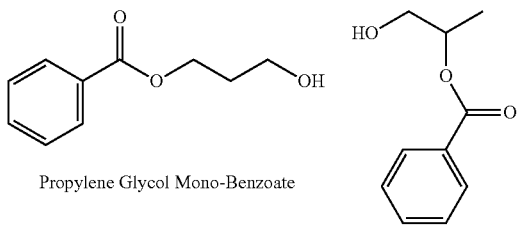

Propylene Glycol Mono-Benzoate

Propylene Glycol Mono-Benzoate

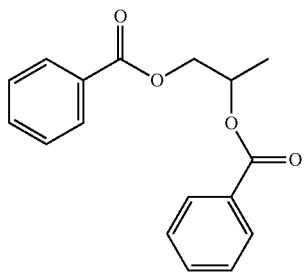

Propylene Glycol Di-Benzoate

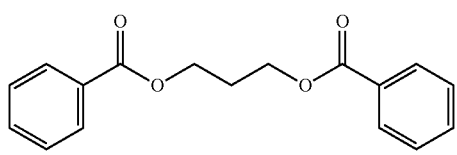

Propylene Glycol Di-Benzoate

12
-continued

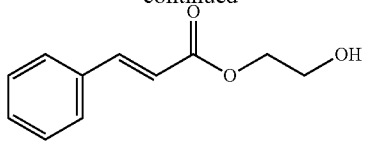

Ethylene Glycol Mono-Cinnamate

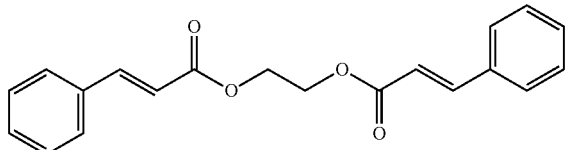

Ethylene Glycol Di-Cinnamate

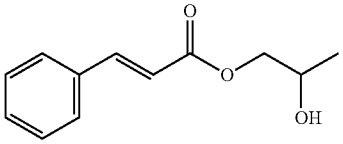

Propylene Glycol Mono-Cinnamate

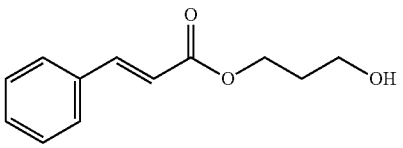

Propylene Glycol Mono-Cinnamate

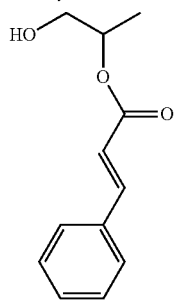

Propylene Glycol Mono-Cinnamate

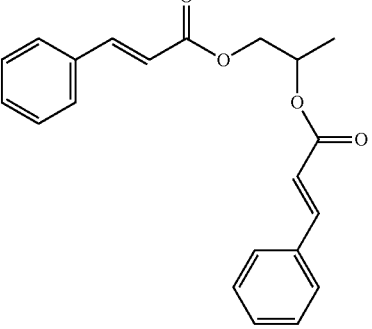

Propylene Glycol Di-Cinnamate

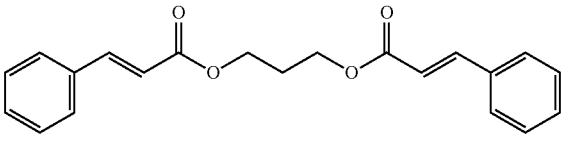

Propylene Glycol Di-Cinnamate

The glycol/acid compounds and derivatives and modifications of the same can be prepared by using convention chemical synthesis techniques (see, e.g., Organic Chemistry, 5$^{th}$ Ed.).

3. Modifications and Derivatives of Glyceryl/Glycol/Acid Compounds

Modifications or derivatives of the glyceryl/acid and glycol/acid compounds disclosed throughout this specification are contemplated as being useful with the methods and compositions of the present invention. Derivatives and modifications may be prepared and the properties of such derivatives and modified compounds may be assayed for their desired properties by any method known to those of skill in the art.

In certain aspects, "derivative" refers to a chemically modified glyceryl/acid or glycol/acid compound that still retains the desired effects of the compound prior to the chemical modification. Such derivatives may have the addition, removal, or substitution of one or more chemical moieties on the glyceryl, glycol, and/or acid portion of the compounds. Non-limiting examples of the modifications that can be made to these portions of the compounds include the addition or removal of alkyl groups, carboxyl groups, carbonyl groups, hydroxyl groups, nitro groups, amino groups, amide groups, azo groups, sulfate groups, sulfonate groups, sulfono groups, sulfhydryl groups, sulfonyl groups, sulfoxido groups, phosphate groups, phosphono groups, phosphoryl groups, and/or halide groups. Additional modifications can include an addition or a deletion of one or more atoms of the atomic framework, for example, substitution of an ethyl by a propyl or substitution of a phenyl by a larger or smaller aromatic group. In a cyclic or bicyclic structure, hetero atoms such as N, S, or O can be substituted into the structure instead of a carbon atom.

B Compositions

The compounds of the present invention can be incorporated into all types of compositions (e.g., cosmetic and pharmaceutical compositions). A person of ordinary skill would recognize that the compositions can include any number of combinations of glyceryl/acid compounds, glycol/acid compounds, and/or additional ingredients, or derivatives thereof. The concentrations of the glyceryl/acid compounds, glycol/acid compounds, and/or additional ingredients, or derivatives thereof, can vary for a given composition. This variation can oftentimes depend on the desired characteristics of the final composition. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the glyceryl/acid compounds, glycol/acid compounds, and/or additional ingredients, or derivatives thereof. In certain non-limiting aspects, the percentages can be calculated by weight or volume of the total composition. A person of ordinary skill in the art would understand that the concentrations can vary depending on the addition, substitution, and/or subtraction of the glyceryl/acid compounds, glycol/acid compounds, and additional ingredients, or derivatives thereof.

C Additional Ingredients

In addition to the glyceryl/acid compounds and/or glycol/acid compounds disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

b. Moisturizers

Non-limiting examples of moisturizing agents that can be used with the compositions of the present invention can be found in the International Cosmetic Ingredient Dictionary, 10$^{th}$ Ed., 2004. Examples include amino acids, chondroitin sulfate, diglycerin, erythritol, fructose, glucose, 1,2,6-hexanetriol, honey, hyaluronic acid, hydrogenated honey, hydrogenated starch hydrolysate, inositol, lactitol, maltitol, maltose, mannitol, natural moisturizing factor, salts of pyrollidone carboxylic acid, potassium PCA, sodium glucuronate, sodium PCA, sorbitol, sucrose, trehalose, urea, and xylitol.

c. Emollients

Non-limiting examples of emollients include, but are not limited to, vegetable oils, mineral oils, silicone oils, synthetic and natural waxes, petrolatum, lanolin, aluminum magnesium hydroxide stearate (which can also function as a water repellent), and fatty acid esters. Non-limiting examples of vegetable oils include safflower oil, corn oil, sunflower seed oil, and olive oil.

d. Antioxidants

Non-limiting examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

e. Thickening Agents

Thickening agents, including thickener or gelling agents, include substances which that can increase the viscosity of a composition. Thickeners include those that can increase the viscosity of a composition without substantially modifying the efficacy of the ingredients within the composition. Thickeners can also increase the stability of the compositions of the present invention. Non-limiting examples of additional thickeners that are known to those of ordinary skill in the art can be used in the context of the present invention (e.g., U.S. Pat. Nos. 5,087,445; 4,509,949; 2,798,053; International Cosmetic Ingredient Dictionary and Handbook, 10$^{th}$ Ed., 2004). Examples include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers include carbomers, which are homopolymers of acrylic acid crosslinked with allyl ethers of sucrose or pentaerytritol (e.g., Carbopol™ 900 series from B.F. Goodrich).

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. The silicon containing compound can be a silicone oil such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in International Cosmetic Ingredient Dictionary, 10$^{th}$ Ed., 2004 as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

2. Pharmaceutical Actives

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D Vehicles

Compositions of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone, water-in-silicone, silicone-in-water emulsions), creams, lotions, solutions (both aqueous and hydro-alcoholic), anhydrous bases (such as lipsticks and powders), gels, and ointments or by other method or any combination of the forgoing as would be known to one of ordinary skill in the art (see, e.g., Remington's, 1990 and International Cosmetic Ingredient Dictionary and Handbook, $10^{th}$ Ed., 2004)). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

E Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

F Kits

Kits are also contemplated as being used in certain aspects of the present invention. For instance, emulsion compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the emulsion composition. In other embodiments, the container can be squeezed (e.g., metal, laminate, or plastic tube) to dispense a desired amount of the emulsion composition. The emulsion composition can be dispensed as a spray, an aerosol, a liquid, a fluid, or a semi-solid. The containers can have spray, pump, or squeeze mechanisms. A kit can also include instructions for employing the kit components as well the use of any other emulsion compositions included in the container. Instructions can include an explanation of how to apply, use, and maintain the emulsion compositions.

EXAMPLES

The following examples are included to demonstrate certain non-limiting aspects of the invention. It should be appreciated by those of skill in the art that the techniques disclosed in the examples which follow representative techniques discovered by the inventor to function well in the practice of the invention. However, those of skill in the art should appreciate that changes can be made in the specific embodiments which are disclosed and still obtain a like or similar result without departing from the spirit and scope of the invention.

Example 1

Methods of Making Glyceryl/Acid or Glycol Acid Compounds

An esterification process can be used for producing glyceryl/acid and glycol/acid compounds. A glyceryl or glycol molecule and an acid molecule are added to a multi-necked round bottom flask equipped with a heating mantle, a condenser, a Dean-Stark trap and a thermometer. A solvent is chosen that will allow a high enough reflux temperature to accommodate the reaction. The reaction is run until the calculated amount of water is collected in the trap signifying that the limiting reagent is exhausted. The by-product can be compounds other than water in some processes. For instance, if a methyl salicylate is used in place of salicylic acid, methanol will be the by-product rather than water, and the methanol may escape through the condenser or remain in the reaction flask. The methanol can be removed when the ester is extracted.

Example 2

UV Absorption Data for Glyceryl Mono-Salicylate

UV absorption data for glyceryl mono-salicylate is summarized in Table 1 below:

TABLE 1

| (UV absorption data*) | |
|---|---|
| Glyceryl Mono-Salicylate | Data |
| Avg. Mol. Wt. | 242.95 |
| Molar Absorptivity ($\lambda$ max 238 nm) | 12065.7 |
| Molar Absorptivity ($\lambda$ max 307 nm) | 6126.4 |

*Data obtained by using a UV/Vis spectrometer using standard USP 197U testing procedures.

Example 3

Compositions

Non-limiting examples of compositions of the present invention are described in Tables 1-3.

TABLE 2*

(Exfoliation composition)

| Ingredient | % Concentration (by weight) |
|---|---|
| SD Alcohol 40-B | 56.00 |
| Glyceryl mono-salicylate** | 7.50 |
| Water | 29.00 |
| Mineral oil | 3.00 |
| Sepigel 305 (thickener) | 4.00 |

*The composition was prepared as follows: Ingredients were cold-mixed and added to a beaker in the listed order prior to the addition of the next ingredient. The pH of the composition was adjusted to approximately 4.3 by using 1N HCl solution.
**Glyceryl mono-salicylate can be substituted with other glyceryl/acid and glycol/acid compounds.

TABLE 3*

(Moisturizer**)

| Ingredient | % Concentration (by weight) |
|---|---|
| Phase A | |
| Water | 66.44 |
| Xanthum gum | 0.10 |
| Methyl paraben | 0.15 |
| Propyl paraben | 0.10 |
| Citric acid | 0.01 |
| Phase B | |
| Cetyl alcohol | 4.00 |
| Glyceryl stearate + PEG 100 | 4.00 |
| Octyl palmitate | 4.00 |
| Dimethicone | 1.00 |
| Tocopheryl acetate | 0.20 |
| Phase C | |
| SD Alcohol 40-B | 15.00 |
| Glyceryl mono-salicylate*** | 5.00 |

*The composition was prepared as follows: Phases A and B were heated to approximately 70° C.-75° C. in separate beakers while mixing. Phase B was added to Phase A when both phases were at approximately 70° C.-75° C. The Phase A + B mixture was cooled to <40° C. while mixing. Phase C was subsequently added to the Phase A + B mixture, and the mixture was cooled to room temperature (approximately 20° C.-25° C.) while mixing.
**Formulation showed statistically significant moisturization for 6 hours after application to skin when compared to the baseline control (p < 0.05) (data not shown).
***Glyceryl mono-salicylate can be substituted with other glyceryl/acid and glycol/acid compounds.

TABLE 4

(Generic formulation)*

| Ingredient | % Concentration (by weight) |
|---|---|
| Phase A | |
| Water | 84.44 |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Glyceryl mono-salicylate** | 2.0 |

*The composition can be prepared as follows: Sprinkle Xanthum gum in water and mix for 10 min. Subsequently, add all ingredients in phase A and heat to 70-75° C. Add all items in phase B to a separate beaker and heat to 70-75° C. Mix phases A and B at 70-75° C. Continue mixing and allow composition to cool to 30° C. Subsequently, add phase C ingredient while mixing.
**Glyceryl mono-salicylate can be substituted with other glyceryl/acid and glycol/acid compounds.

TABLE 5

(Generic formulation)*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Glyceryl mono-salicylate** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Glyceryl mono-salicylate can be substituted with other glyceryl/acid and glycol/acid compounds.

TABLE 6

(Generic formulation)*

| Ingredient | % Concentration (by weight) |
|---|---|
| Phase A | |
| Water | 84.44 |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Glyceryl mono-salicylate** | 1.0 |
| Glycol mono-salicylate** | 1.0 |

*The composition can be prepared as follows: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Glyceryl mono-salicylate and/or glycol mono-salicylate can be substituted with other glyceryl/acid and glycol/acid compounds.

TABLE 7

(Generic formulation)*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |

TABLE 7-continued (Generic formulation)*

| Ingredient | % Concentration (by weight) |
|---|---|
| Phase B | |
| Sepigel 305 | 2.0 |
| Phase C | |
| Glyceryl mono-salicylate** | 1.0 |
| Glycol mono-salicylate** | 1.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Glyceryl mono-salicylate and/or glycol mono-salicylate can be substituted with other glyceryl/acid and glycol/acid compounds.

Example 4

Determining Efficacy of Glyceryl/Acid or Glycol/Acid Compounds and Compositions

The efficacy of the glyceryl/acid or glycol/acid compounds and compositions containing the same can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72 C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman and Gams (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

UV absorption of glyceryl/acid or glycol/acid compounds and compositions containing the same can be determined by UV absorption assays that are generally known to those of ordinary skill in the art.

All of the compounds, compositions, and/or methods disclosed and claimed can be made and executed without undue experimentation in light of the present disclosure. While the compounds, compositions, and methods of this invention have been described in terms of certain embodiments, it will be apparent to those of skill in the art that variations may be applied to the compounds, compositions, and/or methods and in the steps or in the sequence of steps of the method without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

U.S. Pat. No. 2,798,053
U.S. Pat. No. 4,509,949
U.S. Pat. No. 5,087,445
CTFA International Cosmetic Ingredient Dictionary and Handbook, 10th Ed., (2004). Organic Chemistry, 5th Ed.
Packman and Gams, J. Soc. Cos. Chem., 29:70-90, 1978.
Remington's Pharmaceutical Sciences, 18th Ed. Mack Printing Company, 1289-1329, 1990.

The invention claimed is:

1. A method for exfoliating skin in need thereof comprising applying a composition to said skin that includes a glyceryl di-salicylate compound having the following structure:

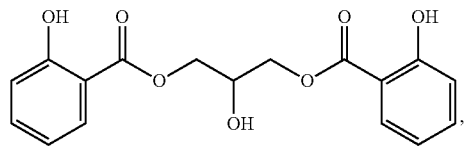

wherein the composition further includes a glyceryl mono-salicylate compound, and wherein the composition exfoliates said skin.

2. The method of claim 1, wherein the composition is applied to melasmic skin.

3. The method of claim 1, wherein the composition is an emulsion, a cream, a lotion, or an ointment.

4. The method of claim 1, wherein the composition comprises from about 0.001 to about 20%, by weight, of the glyceryl di-salicylate and from about 0.001 to about 20%, by weight, of the glyceryl mono-salicylate.

5. The method of claim 1, wherein the glyceryl mono-salicylate has the following structure:

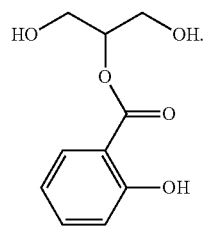

6. The method of claim 1, wherein the composition is applied at least two times to said skin within a twenty-four hour period of time.

* * * * *